(12) United States Patent
Ten Kate et al.

(10) Patent No.: US 10,793,511 B2
(45) Date of Patent: Oct. 6, 2020

(54) PROCESS FOR CONVERTING CYCLIC ALKYLENEUREAS INTO THEIR CORRESPONDING ALKYLENEAMINES

(71) Applicant: NOURYON CHEMICALS INTERNATIONAL B.V., Arnhem (NL)

(72) Inventors: Antoon Jacob Berend Ten Kate, Arnhem (NL); Rens Veneman, Amersfoort (NL); Michiel Jozef Thomas Raaijmakers, Deventer (NL); Slavisa Jovic, Utrecht (NL); Rolf Krister Edvinsson, Partille (SE); Hendrik Van Dam, Ede (NL); Eike Nicolas Kantzer, Uddevalla (SE); Ina Ehlers, Stenungsund (SE); Björn Patrik Skansen, Mölndal (SE); Michael Bertil Einar Andersson-Sarning, Gothenburg (SE); Karl Fredrik Lake, Södertälje (SE); Stig Mikael Wernersson, Södertälje (SE)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 16/638,393

(22) PCT Filed: Aug. 7, 2018

(86) PCT No.: PCT/EP2018/071321
§ 371 (c)(1),
(2) Date: Feb. 11, 2020

(87) PCT Pub. No.: WO2019/030192
PCT Pub. Date: Feb. 14, 2019

(65) Prior Publication Data
US 2020/0199060 A1    Jun. 25, 2020

(30) Foreign Application Priority Data

Aug. 11, 2017 (EP) .................... 17185949

(51) Int. Cl.
| C07C 209/00 | (2006.01) |
| C07C 213/00 | (2006.01) |
| C07C 209/62 | (2006.01) |
| C07C 213/02 | (2006.01) |

(52) U.S. Cl.
CPC .......... $C07C\ 209/62$ (2013.01); $C07C\ 213/02$ (2013.01)

(58) Field of Classification Search
None
See application file for complete search history.

(56) References Cited

U.S. PATENT DOCUMENTS

| 2,812,333 A | 11/1957 | Steele |
| 2,847,418 A | 8/1958 | Steele |
| 4,387,249 A | 6/1983 | Harnden et al. |
| 4,503,250 A | 3/1985 | Herdle |

FOREIGN PATENT DOCUMENTS

GB    878967 A    10/1961

OTHER PUBLICATIONS

EPO, European Extended Search Report issued in European Application No. 17185949.9, dated Oct. 18, 2017.
EPO, International Search Report and Written Opinion issued in International Application No. PCT/EP2018/071321, dated Sep. 26, 2018.

*Primary Examiner* — Sikarl A Witherspoon
(74) *Attorney, Agent, or Firm* — Lorenz & Kopf, LLP

(57) ABSTRACT

A process is provided for converting cyclic alkyleneureas into their corresponding alkyleneamines. The process includes reacting a feedstock comprising cyclic alkyleneureas in the liquid phase with water in an amount of from about 0.1 to about 20 mole water per mole urea moiety, at a temperature of at least 230° C., with removal of CO2. The process may allow the efficient conversion of alkyleneureas into the corresponding alkyleneamines. In certain embodiments, the process has a high yield and low side product production.

18 Claims, 1 Drawing Sheet

Chemical structures
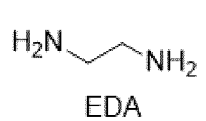
EDA
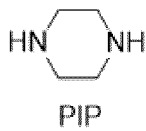
PIP
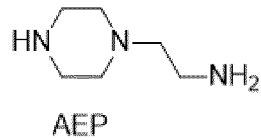
AEP
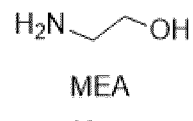
MEA
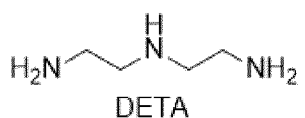
DETA
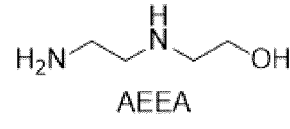
AEEA
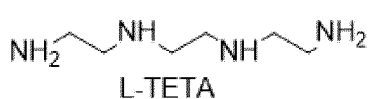
L-TETA
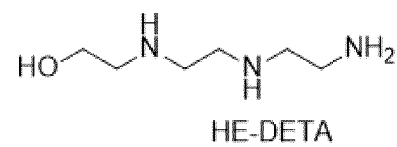
HE-DETA
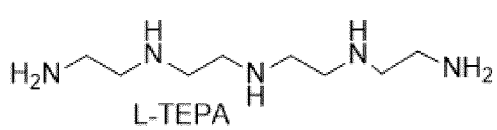
L-TEPA
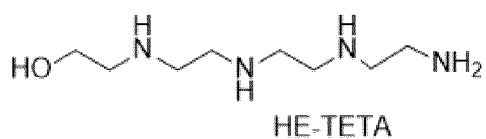
HE-TETA
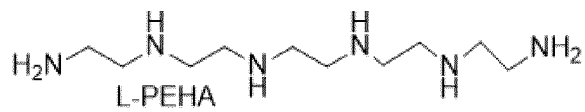
L-PEHA
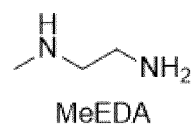
MeEDA
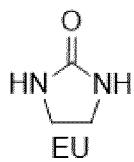
EU
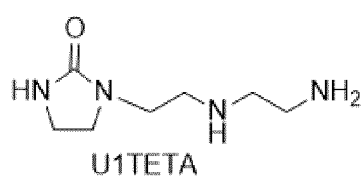
U1TETA
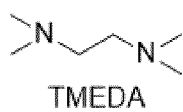
TMEDA
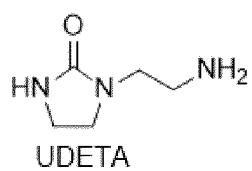
UDETA
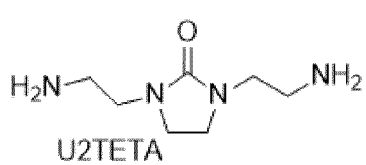
U2TETA
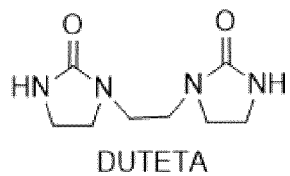
DUTETA
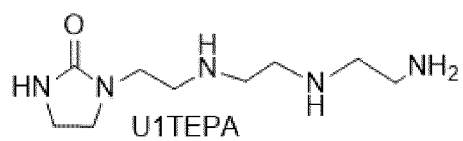
U1TEPA
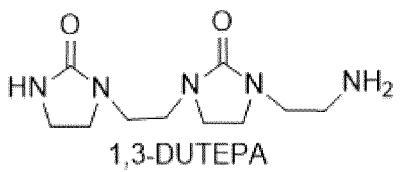
1,3-DUTEPA
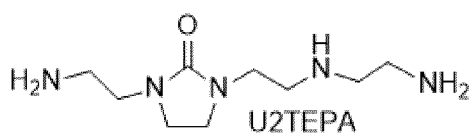
U2TEPA
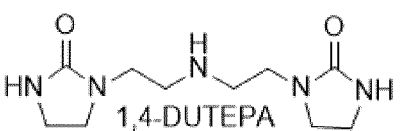
1,4-DUTEPA

PROCESS FOR CONVERTING CYCLIC ALKYLENEUREAS INTO THEIR CORRESPONDING ALKYLENEAMINES

CROSS-REFERENCE TO RELATED APPLICATION

This application is a U.S. National-Stage entry under 35 U.S.C. § 371 based on International Application No. PCT/EP2018/071321, filed Aug. 7, 2018, which was published under PCT Article 21(2) and which claims priority to European Application No. 17185949.9, filed Aug. 11, 2017, which are all hereby incorporated in their entirety by reference.

TECHNICAL FIELD

The present invention pertains to a process for converting cyclic alkyleneureas into their corresponding alkyleneamines.

BACKGROUND

Cyclic alkyleneureas are compounds comprising two nitrogen atoms connected by a carbonyl moiety and an alkylene moiety. For example, cyclic ethyleneurea is a compound comprising a cyclic ethyleneurea moiety in which two nitrogen atoms are connected by a carbonyl moiety and an ethylene moiety, in accordance with the following formula:

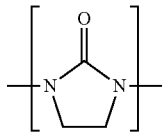

Cyclic alkyleneurea compounds can be converted into the corresponding alkyleneamines by removal of the CO group and addition of two hydrogen atoms. Alkyleneamines, in particular ethyleneamines, specifically in particular diethylene triamine (DETA) and higher ethyleneamines such as (linear) triethylene tetramine (L-TETA) are attractive products from a commercial point of view. Cyclic ethyleneureas are therewith an attractive precursor in the manufacture of ethylenediamine and higher ethyleneamines.

It has been found, however, that cyclic alkyleneureas are relatively stable and difficult to convert to the corresponding alkyleneamines. This can also be seen from the prior art, where the conversion is carried out with large excesses of strong inorganic bases or in the presence of large amounts of water. The difficulty in converting cyclic alkyleneureas into the corresponding alkyleneamines goes in particular for compounds where the alkyleneurea moiety is connected to further alkyleneamine moieties via the nitrogen atoms, in particular where the alkyleneurea moiety is present between two further alkyleneamine moieties.

U.S. Pat. No. 4,503,250 describes a process for preparing linear polyalkylene polyamines which comprises reacting ammonia or an alkyleneamine compound having two primary amino groups or mixtures thereof with an alcohol or an alkanolamine compound having a primary amino group and a primary or secondary hydroxyl group or mixtures thereof in the presence of a derivative of carbonic acid at a temperature at which the reaction will proceed under pressures sufficient to maintain the reaction mixture substantially in a liquid phase. The process results in the formation of urea adducts of polyalkylene polyamines. The urea adducts are converted to polyethylene polyamines by reaction with 50% aqueous KOH under reflux overnight. 8 moles KOH are used per mole carbon dioxide.

U.S. Pat. No. 4,387,249 discloses the reaction of ethylenediamine (EDA), ethanolamine (MEA) and urea to give aminoethylethyleneurea (UDETA) and ethyleneurea (EU), which are hydrolysed to form DETA and EDA. The hydrolysis step takes place in an inert atmosphere in the presence of a Brønsted base. The Brønsted base preferably is the hydroxide of an alkali metal, more preferably an aqueous solution of NaOH. In the examples hydrolysis takes place at a temperature of 200° C. under autogenous pressure, using a 5 mole/liter NaOH solution. The amount of NaOH used can be calculated to correspond to 6.5 mole NaOH per mol-equivalent ethyleneurea moiety. It should be noted that in this reference the compounds to be converted, namely aminoethylethyleneurea (UDETA) and ethyleneurea (EU) are not the difficult-to-convert compounds wherein the alkyleneurea moiety is present between two further alkyleneamine moieties.

U.S. Pat. No. 2,812,333 describes the hydrolysis of 1-(2-hydroxyethyl)imidazolinone-2 to the corresponding hydroxyethylethylenediamine by heating in the presence of water at elevated temperatures, with removal of CO2. The reaction takes place in a large excess of water; in the example a 12% solution of the 1-(2-hydroxyethyl)imidazolinone-2 is used. The conversion is low. Under test conditions approximately 5% of the compound hydrolysed per hour.

GB878,967 indicates that it is known to prepare N-beta-hydroxyethylethylenediamine by hydrolysis with water in an autoclave at 175° C. It is indicated that the process is not very practical with a conversion of 25% in 8 hours. In this reference an alternative process is presented using concentrated sulphuric acid. This process uses a large amount of water and sulphuric acid, and requires subsequent neutralization using a base, in this case CaO.

U.S. Pat. No. 2,847,418 describes hydrolyzing 1,3-di-(2-hydroxyethyl)-imidazolinone-2 to the corresponding amine using a molar equivalent of 5% aqueous NaOH. The amount of water is thus quite large. No further information on the process conditions is provided.

There is need in the art for a process for the conversion of cyclic alkyleneureas into their corresponding alkyleneamines which does not rely on the presence of large amounts of caustic or water, and which can be carried out in an efficient manner. The present invention provides such a process.

BRIEF SUMMARY

A process is provided for converting cyclic alkyleneureas into their corresponding alkyleneamines. The process includes reacting a feedstock comprising cyclic alkyleneureas in the liquid phase with water in an amount of from about 0.1 to about 20 mole water per mole urea moiety, at a temperature of at least 230° C., with removal of CO2.

It has been found that the process according to the invention allows the efficient conversion of alkyleneureas into the corresponding alkyleneamines. The process has a high yield and low side product production. In particular, it has been found that the process according to the invention yields less side product cyclic alkyleneureas where the alkyleneurea moiety is present between two further alkyleneamine moieties on the one hand, and at the same time avoids the use of a strong base and large amounts of aqueous solvent, and so avoids or at least minimizes salt waste streams, corrosion and product degradation. Further advantages of the process according to the invention and specific embodiments thereof will become clear from the further specification.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. Embodiments of the subject matter will be discussed in more detail below.

BRIEF DESCRIPTION OF THE DRAWINGS

The present invention will hereinafter be described in conjunction with the following drawing FIGURES, wherein like numerals denote like elements, and:

FIG. 1 shows the chemical formula of a number of compounds mentioned in the present specification.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

In certain embodiments, numbers in this description indicating amounts, ratios of materials, physical properties of materials, and/or use are may be understood as being modified by the word "about". The term "about" as used in connection with a numerical value and the claims denotes an interval of accuracy, familiar and acceptable to a person skilled in the art. In general, such interval of accuracy is ±10%.

The starting material used in the present invention is a reaction mixture comprising cyclic alkyleneureas. Cyclic alkyleneureas are compounds comprising two nitrogen atoms connected by a carbonyl moiety and an alkylene moiety. For example, in a cyclic ethyleneurea, two nitrogen atoms are connected through a carbonyl moiety and an ethylene moiety in accordance with the following formula:

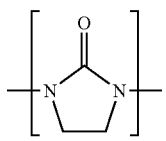

In a preferred embodiment in the process of the invention the cyclic alkyleneurea that is subjected to the conversion to give a corresponding alkyleneamine are:

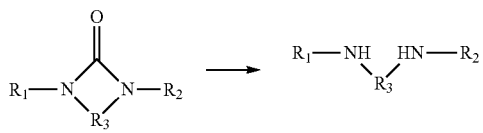

Wherein $R_1$ and $R_2$ each independently are chosen from the group of hydrogen, an alkyleneamine group of the formula X—$R_3$—(NH—$R_3$—)$_p$—, or an alkoxy group of formula X—$R_3$—(O—$R_3$—)$_n$—, or a group combining such alkyleneamine and alkoxy units p and n, wherein one or more units ~N—$R_3$—N~ may be present as either one of the rings

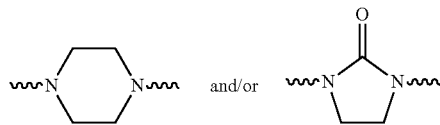

and wherein each $R_3$ independently is as defined below and X may be hydroxyl, amine, a linear or branched C1-C20 hydroxyalkyl or C1-C20 aminoalkyl group, n and p independently is at least 0, preferably 1-20, more preferably 2-20, optionally containing one or more piperazine, or alkyleneurea groups, or when p or n is 0 may be a C1-C20 hydroxyalkyl or C1-C20 aminoalkyl, and $R_3$ is alkylene or substituted alkylene.

In a preferred embodiment $R_2$ is a hydrogen atom and $R_1$ is not a hydrogen atom.

In a more preferred embodiment $R_2$ is a hydrogen atom and $R_1$ is a group that may contain a repeating alkyleneamine group, even more preferably a repeating ethyleneamine group of the formula X—(NH—C2H$_4$)$_n$ wherein optionally one or more units —NH—C$_2$H$_4$—NH— may be present as one of the rings

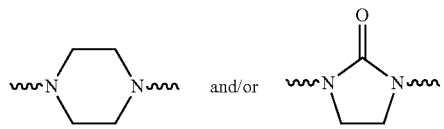

and wherein n is 0 to 20, and X may be a hydrogen atom, an aminoalkyl, an hydroxyalkyl, N-imidazolidinonealkyl or piperazinoalkyl group, or when n is 0a hydroxyalkyl or aminoalkyl, most preferably wherein the alkyl is ethyl.

$R_3$ is preferably ethylene or propylene, optionally substituted with C1-C3 alkyl substituents. More preferably it is an unsubstituted ethylene, unsubstituted propylene or isopropylene, most preferably an unsubstituted ethylene.

Some examples of cyclic alkylene ureas that are most preferred are EU (ethyleneurea), UDETA (the urea of diethylenetriamine), UTETA (the ureas of triethylenetetraamine, i.e. U1TETA or U2TETA, dependent on whether the urea is between the 1$^{st}$ and 2$^{nd}$ amine in the chain or 2$^{nd}$ and 3$^{rd}$ amine, respectively), DUTETA (the diurea of triethylenetetramine), UTEPA (the ureas of tetraethylenepentamine, i.e. U1TEPA, U2TEPA depending on where the urea unit is located), DUTEPA (DU1,3TEPA, DU1,4TEPA, the diureas of tetraethylenepentamine), UAEEA (the urea of aminoethylethanolamine), HE-UDETA (the urea of hydroxyethyl diethylenetriamine, that can exist in two isomers HE-U1DETA and HE-U2DETA), HE-UTETA (the urea of hydroxyethyl triethylenetetraamine, that can exist in three isomers HE-U1TETA, HE-U2TETA and HE-U3TETA), HE-DUTETA (the diurea of hydroxyethyl triethylenetetraamine), or any mixture of these. The molecular structures of a number of the above cyclic alkylene ureas are given in FIG. 1. To avoid any confusion, if a number is given for the amine group where the cyclic urea unit U is located, the amine groups are counted from the terminal amine group on the molecule which in the case of hydroxyethylated ethylene amines is the amine group at the end not containing the hydroxyl group.

The process according to the invention is particularly suitable for converting mixtures of alkyleneamines comprising at least 10 mole % of cyclic urea derivatives of alkyleneamine compounds comprising a —NH—R3-NH—R3-NH—R3-NH— moiety, calculated on the total of cyclic urea compounds present in the mixture. Cyclic urea derivatives of compounds having this moiety are relatively difficult to convert into the corresponding amines, and it is a feature of the process of the present invention that mixtures comprising these compounds can be converted while obtaining a high yield. It may be preferred for the starting material to be a mixture of alkyleneamines comprising at least 15 mole %, in particular at least 20 mole %, of cyclic urea derivatives of alkyleneamine compounds comprising a —NH—R3-NH—R3-NH—R3-NH— moiety, calculated on the total of cyclic urea compounds present in the mixture.

In the process according to the invention, a feedstock comprising cyclic alkyleneureas is reacted in the liquid phase with water in an amount of 0.1-20 mole water per mole urea moiety, at a temperature of at least 230° C., with removal of $CO_2$.

In the process according to the invention, water is used in an amount of 0.1-20 mole water per mole urea moiety present in the starting feedstock. The range of 0.1-20 mole water per mole urea moiety refers to the entire amount of water added during the process, calculated on the amount of urea moieties in feedstock at the start of the reaction. To obtain full conversion, 1 mole water is required per mole urea moiety to be converted. As full conversion is not always necessary, lower amounts of water may be possible. Therefore, water is used in an amount of at least 0.1 mole per mole urea moiety. Higher amounts are often used, e.g., at least 0.2 mole per mole urea moiety, in particular at least 0.5 mole water per mole urea moiety.

It has been found that it is possible in the process according to the invention to obtain good conversion with the relatively limited amount of water of at most 20 mole water per mole urea moiety. It has been found that it possible to work at even lower amounts of water, such as an amount of at most 15 mole water per mole urea moiety, more in particular an amount of at most 10 mole water per mole urea moiety, or even at most 5 mole water per mole urea moiety.

It is preferred for the composition provided to the first step to consist for at least 70 wt. % of the total of water, cyclic alkylene ureas, in particular those indicated above as preferred, and if present, amine compounds selected from the group of primary amines, cyclic secondary amines, and bicyclic tertiary amines, in particular those indicated above as preferred. It is particularly preferred for the composition provided to the first step to consist for at least 80 wt. % of the total of these compounds, more in particular for at least 90 wt. %.

Water can be added at the beginning of the process in a single dosing. It is preferred, however, to add the water during the process, in several dosings or continuously. In a continuous operation multiple feedpoints may be used. By matching the amount of water added to the amount of water consumed by the reaction, the excess water in the reaction mixture can be limited. It has been found that this limits the formation of side products.

The molar ratio of water to urea moieties is calculated on the water present in the liquid reaction medium. If water is added in the form of steam, which may be an attractive embodiment to combine water addition with the provision of heat to the reaction mixture, the majority of water in the steam will not be absorbed in the liquid reaction medium. It is within the scope of the skilled person to regulate the conditions of a water addition process via stream in such a way that the desired amount of water is absorbed by the reaction medium. The water can also be present in the feedstock from the beginning of the reaction, e.g., as a result of the process by which the feedstock was produced. Water can also be added as a liquid.

The reaction is performed at a temperature of at least 230° C. It has been found that at a temperature below this value, the reaction rate is too low to obtain meaningful conversion in an acceptable time frame. It is preferred to carry out the reaction at a temperature of at least 240° C., in particular at least 250°. As a maximum value, a value of 400° C. may be mentioned. It may be preferred to carry out the reaction at a temperature of at most 350° C., in particular at most 320° C.

The pressure during the process is not critical, as long as the reaction medium is in the liquid phase. As a general range, a value of 0.5 to 100 bar may be mentioned, depending on the desired temperature. It is preferred for the $CO_2$ removal step to be carried out at a pressure of at least 5 bar, in particular at least 10 bar, to maintain a sufficient amount of amine and water in the medium. In view of the high costs associated with high-pressure apparatus, it may be preferred for the pressure to be at most 50 bar, in particular at most 40 bar.

$CO_2$ is removed in the process according to the invention. $CO_2$ removal can be carried out when the conversion of the alkyleneureas into ethyleneamine compounds has been completed. However, it is preferred to carry out $CO_2$ removal during the reaction. $CO_2$ removal can be carried out in manners known in the art. The most basic way to do this it to vent the reaction vessel. A stripping fluid, in particular a stripping gas can be used to increase $CO_2$ removal rate. Other measures to improve removal of $CO_2$ will be evident to the skilled person, and include measures like stirring of the reaction mixture, sparging of stripping gas, thin-film evaporation, use of packing or trays, etc.

Where a stripping gas is used, the flow rate is typically at least 1 m3 per 1 m3 reactor volume per hour (at reaction temperature and pressure), and at most 100 m3 per 1 m3 reactor volume per hour (at reaction temperature and pressure). The stripping flow rate can be generated by evaporation of a liquid inside the reactor vessel, resulting in in situ generation of stripping gas. The ranges above also apply to this embodiment. Of course, it is also possible to combine the addition of tripping gas with the in situ formation of stripping gas.

The $CO_2$-containing stripping fluid removed from the $CO_2$ removal step can, for example, comprise from 1 to 99 mol. % $CO_2$. In other embodiments, the stripping fluid may comprise 1-80 mol. % $CO_2$, or 1-60 mol. % $CO_2$. In some embodiments, the effluent from the $CO_2$ removal step may comprise 1-40 mol. % $CO_2$, or 1-20 mol. % $CO_2$. Lower $CO_2$ contents make for more efficient stripping, but also for the use of more stripping gas. It is within the scope of the skilled person to find an appropriate balance between these parameters.

Depending on the reaction temperature and the desired degree of conversion, the reaction time can vary within wide ranges, e.g., at least one minute, in particular at least 5 minutes, more in particular between 15 minutes and 24 hours. In one embodiment, the reaction time may be at least 30 minutes, or at least 1 hour. It may be preferred for the reaction time to vary between 1 hour and 12 hours, in particular between 1 hour and 6 hours. When using lower temperatures, longer reaction times may be required to obtain the desired degree of conversion.

The process according to the invention does not rely on the use of a strong inorganic base. Nevertheless, if so desired, a limited amount of strong inorganic base may be present. Within the context of the present invention, a strong inorganic base is a material which does not contain carbon-carbon bonds and which has a pKb of less than 1. In one embodiment, the strong inorganic base, if used, is selected from the group of metal hydroxides, in particular from the group of hydroxides of alkaline and earth alkaline metals, in particular from sodium hydroxide, potassium hydroxide, lithium hydroxide, calcium hydroxide, magnesium hydroxide, and barium hydroxide. In one embodiment, the strong inorganic base is selected from the group of metal oxides, in particular from the group of oxides of alkaline and earth alkaline metals, in particular from calcium oxide, magnesium oxide, and barium oxide. Selecting a strong inorganic base from the group of sodium hydroxide, potassium hydroxide, magnesium (hydr)oxide, and calcium (hydr)oxide may be preferred. The use of sodium hydroxide and potassium hydroxide may be particularly considered preferred. Other strong inorganic bases may also be used, such as ammonium hydroxide. As will be evident to the skilled person, mixtures of various strong inorganic bases can be used. Compounds comprising a strong base in addition to other components can also be used, as can be compounds which will be converted into strong inorganic bases in the reaction medium. If a strong inorganic base is used, it is generally used in an amount of less than 0.5 mole inorganic base per mole cyclic alkyleneurea moieties, in particular less than 0.2 mole inorganic base per mole cyclic alkyleneurea moieties.

In one embodiment of the present invention the process according to the invention is carried out in the presence of an amine compound selected from the group of primary amines, cyclic secondary amines, and bicyclic tertiary amines. It has been found that increased reaction rates can be obtained.

Primary amines are amine functional compounds in which the amine group is of the formula R4-NH2 and wherein R4 can be any organic group, preferably an aliphatic hydrocarbon with optional heteroatoms such as oxygen and/or nitrogen. Secondary cyclic amines are amines of the formula R5—NH—R6, wherein R5 and R6 together form a hydrocarbon ring, optionally with heteroatoms such as oxygen and/or nitrogen, preferably a piperazine ring. Tertiary bicyclic amines are amines of the formula R7—N(—R9)—R8 where R7 and R8 together form a hydrocarbon ring—optionally with heteroatoms such as oxygen and/or nitrogen—and R7 and R9 together form another hydrocarbon ring—optionally with heteroatoms such as oxygen and/or nitrogen. On all the above groups R4 to R9 substituents can be present, like alkyl or hydroxyalkyl groups. Primary amines, cyclic secondary amine and bicyclic tertiary amines all contain a sterically relatively unhindered amine group. In this document a compound is defined as a primary amine or a secondary cyclic amine or a tertiary bicyclic amine if one of the amine groups in the compound is a primary amine or secondary cyclic amine or a tertiary bicyclic amine group, independent of if this compound contains further amine groups that may be different in their nature. A compound can also contain two or more different amine functionalities, e.g. a primary amine and a secondary cyclic amine functionality or a primary amine, a secondary cyclic amine and a tertiary bicyclic amine functionality.

Preferred examples of primary amines are alkylamines, linear ethylene amines, and alkanolamines. Preferred examples of cyclic secondary amines are amines that contain a terminal piperazine ring. Preferred examples of bicylic tertiary amines are 1,4-diazabicyclo[2.2.2]octane (DABCO), 1,4-diazabicyclo[2.2.2]octan-2-yl)methanol and 1-azabicyclo[2.2.2]octane (Quinuclidine).

The amine compound is preferably a compound with more than one amine group wherein at least one of the amine groups is a primary amine, even more preferably it is an amine wherein two amine groups are a primary amine. The amine compound is preferably a compound different than R1-NH—R3-NH—R2 that is obtained by the process of the invention.

In another preferred embodiment the amine compound is a compound that can bind with the carbonyl group from the cyclic ethylene urea. Preferred amine compounds include an alkylene amine, or an alkanol amine compound, even more preferably a smaller alkylene amine, ethylene amine, or alkanol amine, ethanolamine, than is formed by the process of the invention, most preferably ethylenediamine (EDA), diethylenetriamine (DETA), monoethanolaomine (MEA), aminoethylethanolamine (AEEA), N-aminoethylpiperazine (AEP), N, N'-diaminoethylpiperazine (DAEP), UDETA, N,N'-diaminoethyl-2-imidazolidinone (U2TETA), tris-aminoethylamine (TAEA).

In yet another preferred embodiment the amine compound is a compound that binds the carbonyl group from the cyclic alkylene urea to give among others another linear or cyclic alkylene urea or linear or cyclic alkylene carbamate, that is larger or less volatile than the alkylene amine formed by the process of the invention, even more preferably an ethylene amine that is solid under the conditions used to work up the reaction mixture or an ethylene amine bound to a solid carrier. Examples thereof are DETA-PS (i.e. a diethylene triamine linked to a solid polystyrene) or a solid polyethyleneimine (PEI).

Preferred amine compounds that can be used in the CO2 removal step of the process according to the invention include ethylenediamine (EDA), N-methylethylenediamine (MeEDA), diethylenetriamine (DETA), ethanolamine (MEA), aminoethylethanolamine (AEEA), piperazine (PIP), N-aminoethylpiperazine (AEP), 1,4-diazabicyclo[2.2.2]octane (DABCO), 1,4-diazabicyclo[2.2.2]octan-2-yOmethanol, triethylenetetramine (TETA), N-diethyldiamine-2-imidazolidinone (U1TETA), N, N'-diaminoethylpiperazine (DAEP), N-[(2-aminoethyl)2-aminoethyl]piperazine) (PEEDA), the cyclic urea of PEEDA (UPEEDA), N, N'-diaminoethyl-2-imidazolidinone (U2TETA), tetraethylenepentamine (TEPA), pentaethylenehexamine (PEHA), and the mono cyclic ureas of TEPA and PEHA (i.e. U1TEPA, U2TEPA, U1PEHA, U2PEHA, U3PEHA) and the dicyclic urea isomers of PEHA (i.e. DUPEHA), a polyethyleneimine (PEI) or an alkylene amine on a solid carrier.

The amine compound, if used, is preferably dosed in a molar amount of between 0.001 and 100 equivalents in regard to the total molar amount of cyclic ethylene urea, more preferably between 0.01 and 50 equivalents, even more preferably between 0.05 and 30 equivalents, yet more preferably between 0.15 and 25 equivalent and most preferably between 0.20 and 20 equivalents.

The process according to the invention results in the formation of a reaction mixture comprising alkylene amines, preferably ethylene amines.

The process according to the invention can be carried out in batch operation, fed-batch operation, or in a continuous operation, e.g., in a cascade of continuous flow reactor. Depending on the scale of the operation, continuous operation may be preferred.

The present invention will be elucidated by the following examples, without being limited thereto or thereby.

Example 1: Conversion of DUTETA at a Water to Urea Ratio of 4:1

The experimental set-up used in the experiment described below was a pressure vessel with a volume of 2000 ml equipped with a condenser, a pressure regulator, a gas distributor and a mixer. The pressure in the reaction vessel and the condenser was kept constant at 30 bara using the pressure regulator. The top temperature of the condenser was kept between 30 and 60° C. During the reaction the mixture was continuously stirred and a constant flow of N2 gas was supplied to the reactor vessel using the gas distributor. Gasses or vapors that were produced or fed to the system during the reaction in excess of 30 bara were allowed to escape the reactor via the condenser and the pressure regulator.

A reaction mixture was prepared by mixing 430 grams of DUTETA and 300 grams of H2O. The molar ratio of $H_2O$ to urea moieties was 4:1. The mixture was kept at 270° C. for 5.4 hours in the reactor described above. The N2 gas flow used was ~2 L/min. Analysis by gas chromatography using a flame ionization detector (GC-FID analysis) showed that the conversion of DUTETA into L-TETA was 54% and that 70% of the initial urea-groups were removed from the system. The CO2 removal rate was 0.54 mol/kg/hour.

This example shows that it is possible to convert DUTETA into L-TETA in the presence of limited amounts of water.

Examples 2-4: Conversion of DUTETA at Different Water to Urea Ratios

Example 1 was repeated at different water to urea ratios in the same experimental set-up. The reaction time was selected such in each experiment that the removal rate could be calculated with reasonable accuracy. The results are presented in table 1.

TABLE 1

|  | Example 1 | Example 2 | Example 3 | Example 4 Comp |
|---|---|---|---|---|
| H$_2$O/U (mol/mol) | 4 | 10 | 1 | 50 |
| Pressure (bar) | 35 | 34 | 34 | 34 |
| Temperature (C.) | 270 | 270 | 270 | 270 |
| Reaction time (hr) | 5.3 | 6.7 | 19.2 | 6.6 |
| N$_2$ flow (L/min) | 2 | 2 | 2 | 2 |
| Results |  |  |  |  |
| Removal rate (mol/kg/hr) | 0.54 | 0.39 | 0.22 | 0.11 |
| U-removal | 70% | 73% | 49% | 73% |
| L-TETA yield | 54% | 51% | 21% | 25% |
| Selectivity (L-TETA yield/U-removal) | 77% | 71% | 44% | 34% |

In Table 1, Examples 1, 2, and 3 are according to the invention. They show that operation at water to urea moiety molar ratios of 4:1, 10:1, and 1:1 result in a substantial removal of urea groups with a good selectivity to L-TETA. Contrary to expectations, the presence of more water in Comparative Example 4 (H2O/U molar ratio is 50:1) leads to a lower selectivity for L-TETA, and also to a lower removal rate.

Example 5: Conversion of UDETA at a Water to Urea Ratio of 4:1

In the experimental set-up as described in Example 1, a reaction mixture was prepared by mixing 350 grams of UDETA and 191 grams of $H_2O$. The molar ratio of $H_2O$ to urea moieties was 4:1. The mixture was kept at 270° C. for 5.8 hours in the reactor described above. The N2 gas flow used was ~4 L/min. Analysis by gas chromatography using a flame ionization detector (GC-FID analysis) showed that the conversion of UDETA into DETA was 55% and that 60% of the initial urea-groups were removed from the system. The average removal rate was 0.62 mol/kg/hr.

Example 6: Conversion of UAEEA at a Water to Urea Ratio of 4:1

In the experimental set-up as described in Example 1, a reaction mixture was prepared by mixing 350 grams of UAEEA and 188 grams of $H_2O$. The molar ratio of $H_2O$ to urea moieties was 4:1. The mixture was kept at 250° C. for 4.2 hours in the reactor described above. The N2 gas flow used was ~2 L/min.

Analysis by gas chromatography using a flame ionization detector (GC-FID analysis) showed that the conversion of UAEEA into AEEA was 42% and that 38% of the initial urea-groups were removed from the system. The average removal rate was 0.45 mol/kg/hr.

Example 7: Conversion of UAEEA at a Water to Urea Ratio of 0.5:1

In the experimental set-up as described in Example 1, a reaction mixture was prepared by mixing 500 grams of UAEEA and 33 grams of $H_2O$. The molar ratio of $H_2O$ to urea moieties was 0.5:1. The mixture was kept at 250° C. for 4.25 hours in the reactor described above. The N2 gas flow used was ~1.5 L/min. Gasses or vapors that were produced or fed to the system during the reaction in excess of 20 bara were allowed to escape the reactor via the condenser and the pressure regulator.

Analysis by gas chromatography using a flame ionization detector (GC-FID analysis) showed that the conversion of UAEEA into AEEA was 13% and that 13% of the initial urea-groups were removed from the system. The average removal rate was 0.23 mol/kg/hr.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for converting cyclic alkyleneureas into their corresponding alkyleneamines, the process comprising reacting a feedstock comprising cyclic alkyleneureas in the liquid phase with water in an amount of from about 0.1 to about 20 mole water per mole urea moiety, at a temperature of at least about 230° C., with removal of CO2.

2. The process according to claim 1 wherein the cyclic alkyleneurea reacts to an alkyleneamine in accordance with below reaction

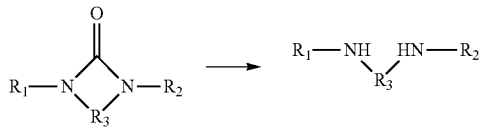

wherein $R_1$ and $R_2$ each independently are chosen from the group of hydrogen, an alkylene amine group of the formula X—$R_3$—(NH—$R_3$—)p—, or an alkoxy group of formula X—$R_3$—(O—$R_3$—)n—, or a group combining such alkylene amine and alkoxy units p and n, wherein optionally one or more units ~N—$R_3$—N~ may be present as either one of the rings

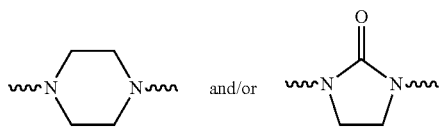

and wherein each $R_3$ independently is as defined below and X may be hydroxyl, amine, a linear or branched C1-C20 hydroxyalkyl or C1-C20 aminoalkyl group, n and p independently is at least 1, optionally containing one or more piperazine, or alkylene urea groups, or when p or n is 0 may be a C1-C20 hydroxyalkyl or C1-C20 aminoalkyl, and $R_3$ is alkylene or substituted alkylene.

3. The process according to claim 2 wherein $R_2$ is a hydrogen atom.

4. The process of claim 1, wherein $R_3$ is ethylene, propylene, or isopropylene, in particular ethylene.

5. The process of claim 1, wherein the cyclic alkyleneurea comprises one or more of EU (ethyleneurea, the urea derivative of ethylenediamine (EDA)), UDETA (the urea derivative of diethylenetriamine (DETA)), UTETA (the group of urea derivatives of triethylenetetraamine (TETA), DUTETA (the diurea derivative of triethylenetetramine), UTEPAs (the urea derivatives of tetraethylenpentamine (TEPA)), DUTE-PAs (the diurea derivatives of TEPA), or urea derivatives of pentaethylenehexamine (PEHA) and higher analogues, UAEEA (the urea derivative of aminoethylethanolamine), HE-UDETA (the urea derivative of hydroxyethyl diethylenetriamine), HE-UTETA (the urea derivative of hydroxyethyl triethylenetetraamine, HE-DUTETA (the diurea derivative of hydroxyethyl triethylenetetraamine), or any mixture of these.

6. The process of claim 1, wherein the feedstock comprises at least about 10 mole % of cyclic urea derivatives of alkyleneamine compounds comprising a —NH—$R_3$—NH—$R_3$—NH—$R_3$—NH—moiety, calculated on the total of cyclic urea compounds present in the mixture.

7. The process of claim 1, wherein the molar ratio of water to urea moieties is at most about 15 mole water per mole urea moiety.

8. The process of claim 1, wherein the water is added in several dosings or continuously during the process.

9. The process of claim 1, wherein the reaction is carried out at a temperature of from about 240° C. to about 400° C.

10. The process of claim 1, wherein CO2 is removed during the reaction.

11. The process of claim 1, wherein the reaction is carried out for a reaction time of from about 15 minutes to about 24 hours.

12. The process of claim 1 wherein the reaction is carried out at a temperature of from about 250° C. to about 320° C.

13. The process of claim 1 wherein the feedstock comprises at least about 15 mole % of cyclic urea derivatives of alkyleneamine compounds comprising a —NH—$R_3$—NH—$R_3$—NH—$R_3$—NH—moiety, calculated on the total of cyclic urea compounds present in the mixture.

14. The process of claim 1 wherein the feedstock comprises at least about 20 mole % of cyclic urea derivatives of alkyleneamine compounds comprising a —NH—$R_3$—NH—$R_3$—NH—$R_3$—NH—moiety, calculated on the total of cyclic urea compounds present in the mixture.

15. The process of claim 1 wherein the molar ratio of water to urea moieties is at most about 10 mole water per mole urea moiety.

16. The process of claim 1 wherein the molar ratio of water to urea moieties is at most about 5 mole water per mole urea moiety.

17. The process of claim 1, wherein $R_3$ is ethylene.

18. The process of claim 2, wherein n and p independently is 2-20.

* * * * *